United States Patent [19]

Poveromo

[11] Patent Number: 4,573,923
[45] Date of Patent: Mar. 4, 1986

[54] DENTURE CONNECTOR
[75] Inventor: Melvin D. Poveromo, Miami, Fla.
[73] Assignees: George Poveromo; March Poveromo; Melanie Poveromo, all of Bay Harbor Islands, Fla.
[21] Appl. No.: 614,078
[22] Filed: May 25, 1984
[51] Int. Cl.[4] .............................................. A61C 13/22
[52] U.S. Cl. .................................... 433/181; 433/182
[58] Field of Search ........................ 433/181, 182, 183
[56] References Cited
U.S. PATENT DOCUMENTS

| | | | |
|---|---|---|---|
| 866,304 | 9/1907 | Roach | 433/183 |
| 1,297,199 | 3/1919 | McAuley | 433/181 |
| 1,297,561 | 3/1919 | Guntner | 433/181 |
| 1,324,476 | 12/1919 | Supplee | 433/181 |
| 1,520,809 | 12/1924 | Cohen | 433/181 |
| 1,693,845 | 12/1928 | Kellner et al. | 433/182 |
| 3,117,377 | 1/1964 | Poveromo | 433/182 |
| 4,196,516 | 4/1980 | Poveromo | 433/182 |
| 4,362,509 | 12/1982 | Sulc | 433/181 |

Primary Examiner—John J. Wilson
Attorney, Agent, or Firm—Sughrue, Mion, Zinn, Macpeak and Seas

[57] ABSTRACT

A denture attachment comprises a hollow cylindrical female member having a laterally extending web portion and a retention plate for embedding in a denture crown. A male member having a non-metal sleeve adapted to be inserted in the female member for rotation therein. The male member has a laterally projecting attachment arm for attaching the male member to adjacent denture material.

11 Claims, 11 Drawing Figures

U.S. Patent   Mar. 4, 1986   Sheet 1 of 3   4,573,923
FIG. 1.
FIG. 2.
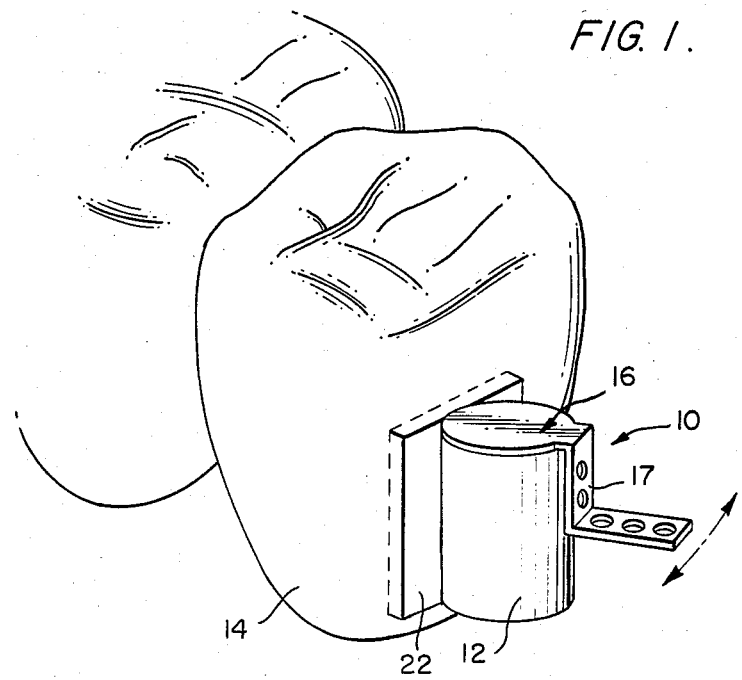
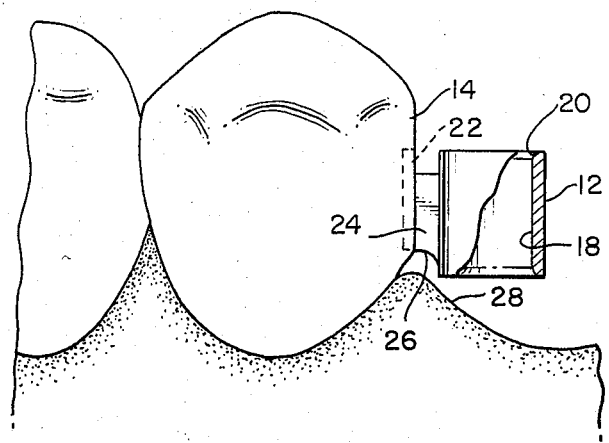
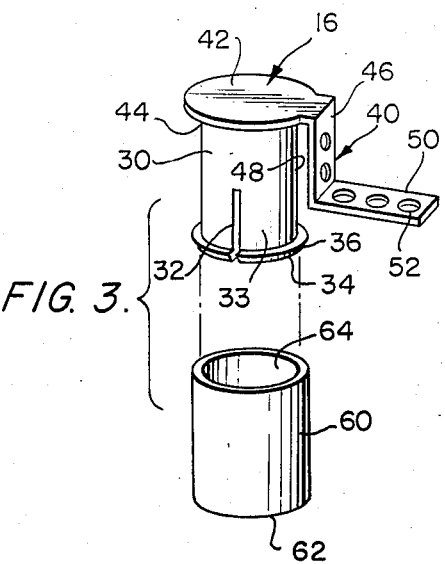
FIG. 3.

DENTURE CONNECTOR

BACKGROUND OF THE INVENTION

1. Field of the Invention

This invention pertains to a connector for dentures which includes a female member, a male member and a plastic insert.

2. Statement of the Prior Art

The prior art shows denture connector or attachment devices comprising male and female metal members. None of these prior art devices discloses a denture attachment comprising a female member, a male member having a plastic sleeve for insertion into the female member and means for expanding the male member as wear occurs on the plastic sleeve.

It is one object of this invention to provide a denture connector or attachment which is simple and inexpensive to construct and install.

It is a further object of this invention to provide a denture attachment or connector wherein the female member comprises a hollow cylinder having a web attached to the outer wall thereof and further having a retention plate attached to the web which is embedded in the crown of a tooth. The lower edge of the web has a curvature to accommodate the crest of the gingiva.

It is another object of this invention to provide a male member comprising a solid cylinder which has a flanged edge for easy insertion into the female member. The male member is provided with at least one slit in an end thereof whereby the cylinder may be compressed upon the application of pressure thereto.

Yet another object of this invention is to provide a male member with an extension shank member whereby the male member may be rotated when positioned inside the female member and whereby the male member may be attached to adjacent denture material.

It is yet another object of this invention to provide the male member with an outer plastic sleeve which functions as a friction and bearing surface when the male member and sleeve are positioned within the female member.

And still a further object of this invention is to provide means to expand the male member which comprises at least one slit in an end of the male member through the diameter thereof and a tapered recess to accommodate an expansion member.

And yet another object of this invention is to provide a male member in the form of a screw which is threaded into an extension shank member.

These and other objects of this invention will become more apparent from a review of the specification, when taken in light of the annexed drawings.

BRIEF DESCRIPTION OF THE DRAWINGS

FIG. 1 is a perspective view of the invention showing a female member having a retention plate which is embedded in a crown and a male member rotatable in the female member and having a connector for attachment of adjacent denture.

FIG. 2 is a side view of the female member which is a hollow cylinder attached to the crown by a retention plate.

FIG. 3 is an exploded view of the male member with a laterally projecting connector arm and a plastic insert.

DESCRIPTION OF THE PREFERRED EMBODIMENT

Figure 4:
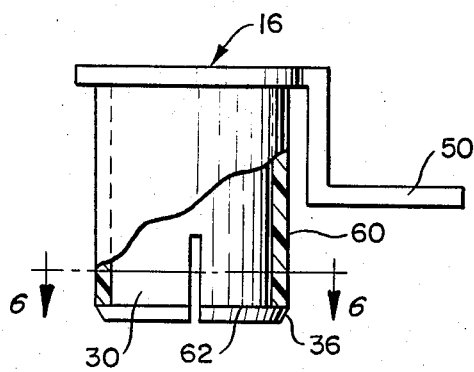
FIG. 4 is a perspective view of the male member showing the plastic sleeve thereon.

Referring now in more detail to the drawings, FIG. 1 shows a denture connector 10 comprising a female member 12 attached to the crown of a denture 14 and a male member 16 having an attachment shank 17 for attaching the male member to adjacent denture area.

The female member, FIG. 2, comprises a cylindrical portion 18 having an outwardly flared upper edge 20. The cylindrical portion 18 is attached to a denture crown 14 by a retainer plate 22 and an intermediate web portion 24. The bottom edge of the web portion 24 is curved at 26 to accommodate the crest 28 of the gingiva which is generally elevated next to the crown.

The male member 16, FIG. 3, comprises a solid cylindrical member 30 having a slit 32 extending across the diameter thereof and extending vertically approximately one half the height of the member 30. The male member has a flared bottom edge 34 and a protruding lip 36, the purposes of which will be explained below.

The male member 16 has an attachment member 40 comprising an upper planar portion 42 which is secured to the upper edge 44 of the male member 30, a vertical portion 46 distal from the outer wall 48 of the male member 30 and a lateral arm 50 in which there are a number of apertures 52. The arm 50 facilitates rotation of the male member within the female member and also facilitates attachment of the male member to the adjacent denture area. The apertures in the arm 50 receive some of the denture material thus insuring a strong bond.

In FIG. 4, the plastic sleeve 60 is shown as being slightly smaller in height than the height of the cylinder member 30 and also slightly smaller in inner diameter than the outer diameter of the cylinder member 30. To insert the plastic sleeve, merely compress the bottom area of the male cylinder 30 which will yield due to the slit and slip the plastic sleeve onto the cylinder 30 until the lip 36 engages the bottom edge 62 of the sleeve. Release of the male member will cause the bottom portion 33 to expand thus engaging the inner wall 64 of the sleeve 60 in a tight grip.

Figure 5:
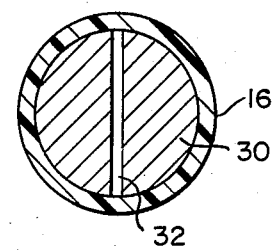
FIG. 5 shows the bottom of the male member having a slit and a plastic sleeve over the male member.
Figure 6:
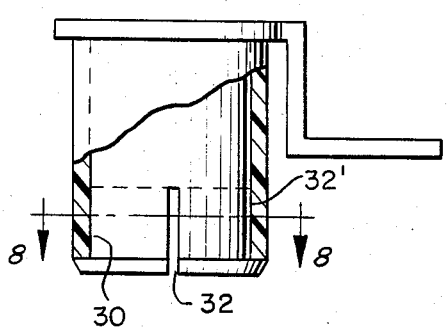
FIG. 6 is a view of the male member and the plastic sleeve.
Figure 7:
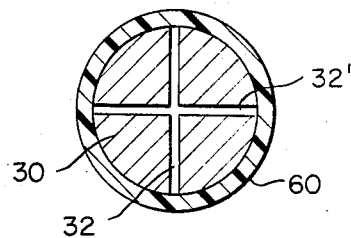
FIG. 7 shows the bottom of the male as having a double slit.

The male member 16 with the sleeve attached is then inserted into the hollow cylindrical female member 12. Insertion of the male member into the female member is made easy by the flared bottom edge 34 of the male member and the flared upper edge 20 of the female member. When the male member with the sleeve thereon is in position in the female member, the male member and sleeve are readily rotatable by manipulation of the lateral arm 50. Easy rotation of the male member within the female member is desirable so as to provide optimum positioning of the lateral arm 50 over the crest of the gingiva. FIG. 5 shows an end view of the assembled components 30 and 60 and the slit 32. FIGS. 6 and 7 show a modification in that the cylinder 30 has a double slit 32 and 32' for easy compression of the bottom of the cylinder 30.

FIG. 4 shows the plastic sleeve 60 in position on the cylinder member 30 with the lip 36 engaged against the bottom edge 62 of the plastic sleeve.

Figure 8:
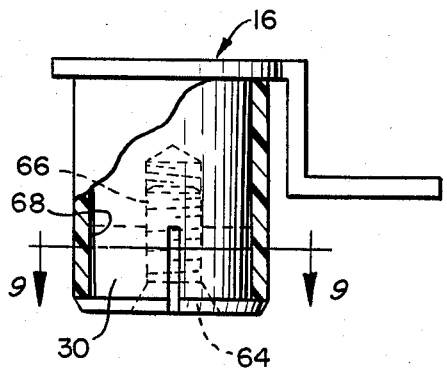
FIG. 8 is a perspective view of the male member and shows an expansion screw extended into the end thereof.
Figure 9:
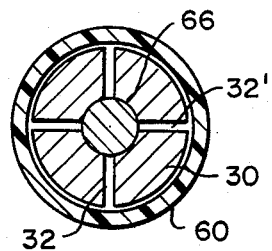
FIG. 9 is an exploded view of another embodiment of the male member, plastic sleeve and shank connector member.

In the embodiment of FIG. 8, the male member 16 is constructed so that the cylinder 30 tapers downwardly and inwardly whereby the outer diameter of the cylinder 30 is slightly smaller than the inner diameter of the sleeve 60. When the sleeve is fitted over the male cylinder 30, a screw 64 is threaded into a recess 66 in the cylinder 30 thus expanding the male cylinder 30 against the inner wall 68 of the sleeve 60. Should the sleeve 60 become worn or loose during use, it is only necessary to continue inward rotation of the screw 64 to further expand the male cylinder 30 against the sleeve 60. When the sleeve becomes totally worn or damaged, it is removed from the male cylinder 30 and replaced by a new sleeve.

Figure 11:
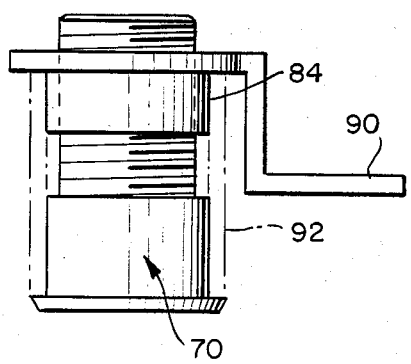
FIG. 11 is a perspective view of the assembled connection.
Figure 10:
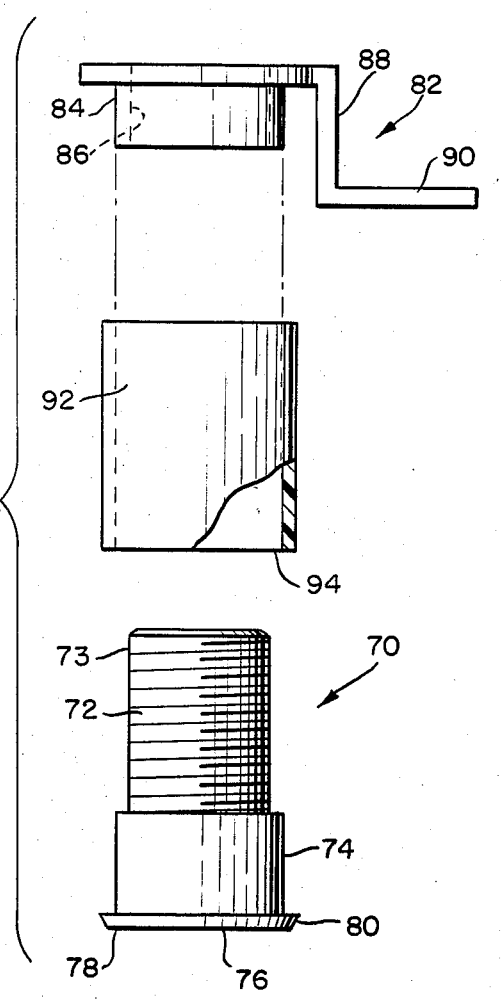
FIG. 10 is an exploded view of the male member, plastic sleeve and shank connector member.

In FIG. 10 there is shown a modified embodiment of the invention wherein the male cylinder is a screw 70 having a threaded portion 72, a shank portion 74 and a base portion 76 having a lip 78 which is flared at 80. The attachment member 82 comprises a hollow shank portion 86 having internal threads 96 to receive the threaded end 73 of the screw 70. The connector has a vertical section 88 and a lateral arm 90 which is embedded in adjacent denture material. The nylon sleeve 92 is telescoped onto the shank portion 84. The threaded end 73 and shank 74 of the screw 70 are telescoped into the sleeve and threaded into the shank 84 until the lip 78 engages the edge 94 of the sleeve. The assembled screw 70, shank 84 and plastic sleeve 92 are shown in FIG. 11.

While the invention has been described in detail with respect to a preferred embodiment thereof, it will be appreciated by those skilled in the art to which the invention pertains that numerous changes may be made in the invention without departing from the spirit and scope thereof.

We claim:
1. A denture connector comprising:
   a female member attached to a denture crown by a web portion having a curved edge to accommodate the crest of the gingiva;
   a male member adapted to be received in the female member for rotation therein, said male member having at least one slit in the end thereof, said slit extending through the diameter of the male member and extending approximately one half its height, whereby the end of the male member may be compressed;
   a sleeve for attachment to the male member after compression of said male member; and
   an attachment member extending from the male member for attaching the male member to adjacent denture material.
2. A denture connector according to claim 1, and:
   said sleeve has a lower edge and said male has a lower tapered edge and a protruding lip which projects beyond the lower edge of the sleeve when same is inserted onto the male thus retaining the sleeve in place.
3. A denture connector according to claim 1, wherein:
   said sleeve is plastic.
4. A denture connector according to claim 1, wherein:
   said sleeve is nylon.
5. A denture connector according to claim 1, wherein:
   said sleeve is replaceable when worn.
6. A denture connector according to claim 1, wherein:
   said attachment member comprises a top planar part attached to a top edge of the male member, a vertical depending part spaced from the outer wall of the male member and a laterally projecting arm for attachment to adjacent denture material.
7. A denture connector according to claim 6, and:
   said laterally projecting arm has a plurality of apertures to receive denture material thus insuring a strong bond in the adjacent denture material.
8. A denture connector comprising:
   a female member attached to a denture crown by a web portion having a curved edge to accommodate the crest of the gingiva;
   a male member having a threaded portion and a non-threaded portion;
   a sleeve for attachment to the male member;
   said male member and sleeve to be inserted into the female member; and
   an attachment member on the male member having a shank portion at one end and a laterally extending arm on the other end for attaching the male member to adjacent denture material.
9. A denture connector according to claim 8, wherein:
   said shank portion of the attachment member comprising a hollow member with internal threads to receive the threaded portion of the male member.
10. A denture connector according to claim 8, wherein:
   said male member has a threaded portion, a non-threaded portion and a base portion having a protruding lip to seat against an edge of said sleeve.
11. A denture connector according to claim 8, wherein:
   said non-threaded portion of the male member and said shank portion of the attachment member being of equal diameter to snugly grip the inside wall of the sleeve.

* * * * *